United States Patent [19]

Krähmer et al.

[11] Patent Number: 4,591,376
[45] Date of Patent: May 27, 1986

[54] 1,2,3-THIADIAZOL-3-IN-5-YLIDENE-UREA DERIVATIVES, METHODS FOR THE PRODUCTION OF THESE COMPOUNDS AS WELL AS COMPOSITIONS CONTAINING THE SAME AND HAVING GROWTH-REGULATORY AND DEFOLIATING ACTIVITY

[75] Inventors: Hansjörg Krähmer; Reinhart Rusch; Hans-Rudolf Krüger; Volkert Sjut, all of Berlin, Fed. Rep. of Germany

[73] Assignee: Schering Aktiengesellschaft, Berlin, Fed. Rep. of Germany

[21] Appl. No.: 612,444

[22] Filed: May 21, 1984

[30] Foreign Application Priority Data

May 20, 1983 [DE] Fed. Rep. of Germany ....... 3319008

[51] Int. Cl.$^4$ .................... C07D 285/06; A01N 47/36
[52] U.S. Cl. .......................................... 71/90; 548/127
[58] Field of Search ............................. 548/127; 71/90

[56] References Cited

U.S. PATENT DOCUMENTS 4,358,596 11/1982 Krüger ................................ 548/127

FOREIGN PATENT DOCUMENTS 2745968 4/1979 Fed. Rep. of Germany ...... 548/127

Primary Examiner—Robert Gerstl
Attorney, Agent, or Firm—Michael J. Striker

[57] ABSTRACT

New 1,2,3-thiadiazol-3-in-5-yliden-urea derivatives are disclosed of the general formula

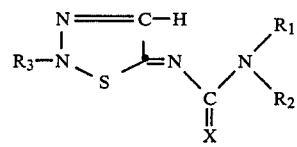

in which $R_1$ is hydrogen or an, if necessary, interrupted one or more times oxygen or sulfur atom, $C_1$–$C_4$-alkyl group, $R_2$ is an, if necessary interrupted one or more times by oxygen or sulfur atoms $C_1$–$C_4$-alkyl group, an, if necessary, substituted one or more times by alkyl $C_3$–$C_8$ cycloalkyl group, an, if necessary, substituted one or more times by alkyl and/or halogen and/or alkylthio and/or alkoxy and/or trifluoromethyl and/or nitro aromatic hydrocarbon group or an, if necessary, substituted heterocyclic, at least one N-atom-containing, hydrocarbon group or $R_1$ and $R_2$ together with the N-atom are morpholino-, piperidino- or pyrolidino-, $R_3$ is an, if necessary, substituted $C_1$–$C_{10}$-alkyl group, a $C_2$–$C_6$-alkenyl, or $C_3$–$C_6$-alkenyl group, or an, if necessary, substituted aryl-$C_1$–$C_2$-alkyl group and X is an oxygen or a sulfur atom, as well as its acid addition salt with inorganic and organic acid. Also disclosed are processes for the production of these compounds and compositions containing the same and having growth-regulatory and defoliating activity.

16 Claims, No Drawings

1,2,3-THIADIAZOL-3-IN-5-YLIDENE-UREA DERIVATIVES, METHODS FOR THE PRODUCTION OF THESE COMPOUNDS AS WELL AS COMPOSITIONS CONTAINING THE SAME AND HAVING GROWTH-REGULATORY AND DEFOLIATING ACTIVITY

BACKGROUND OF THE INVENTION

The invention concerns new 1,2,3-thiadiazol-3-in-5-ylidene-urea derivatives, processes for the production of these compounds, as well as compositions containing the same and having the growth-regulatory and defoliating activity.

1,2,3-thiadiazol-urea derivatives with growth-regulatory and defoliating activity are already known. (See, e.g., DE-OS-2214632 and DE-OS-2506690.) Despite the fact that products of this type have been known in practice, there exists moreover, a need for compounds displaying greater intensity of effectiveness and speed of activity.

SUMMARY OF THE INVENTION

It is, therefore, an object of the present invention to provide new 1,2,3-thiadiazol-urea derivatives which surpass structurally analgous compounds of the same direction of activity with regard to their intensity of activity and speed of activity.

This object is obtained according to the present invention by 1,2,3-thiadiazol-3-in-5-ylidene-urea derivatives of the general formula

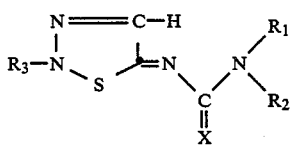

in which $R_1$ is hydrogen or an, if necessary, interrupted one or more times oxygen or sulfur atom, $C_1-C_4$-alkyl group, $R_2$ is an if necessary interrupted one or more times by oxygen or sulfur atoms $C_1-C_4$-alkyl group, an if necessary substituted one or more times by alkyl $C_3-C_8$ cycloalkyl group, an if necessary substituted one or more times by alklyl and/or halogen and/or alkylthio and/or alkoxy and/or trifluoromethyl and/or nitro aromatic hydrocarbon group or an if necessary substituted heterocyclic, at least one N-atom-containing, hydrocarbon group or $R_1$ and $R_2$ together with the N-atom-are morpholino-, piperidino- or pyrolidino, $R_3$ is an if necessary sutstituted $C_1-C_{10}$-alkyl group, a $C_2-C_6$-alkenyl, or $C_3-C_6$-alkenyl group, or an if necessary substituted aryl-$C_1-C_2$-alkyl group and X is an oxygen or a sulfur atom, as well as its acid addition salt with inorganic and organic acid.

The compounds according to the present invention are suitable in outstanding manner for the defoliation of plants, preferably cotton plants, and surpass in this regard and in surprising manner the known agents of analogous constitution.

Aside from cotton cultures, the compounds according to the present invention are advantageously employed even in tree-nurseries, fruit cultures and with legumes. The plants or plant parts to be harvested are thereby in advantageous manner not only made more easily accessible but also are considerably accelerated in their ripening. With appropriate environmental conditions the so-treated plants subsequently again form healthy, normal foliage.

The compounds according to the present invention display moreover, a characteristics cytokinine activity, wherein they likewise surpass the known cytokinines in suprising manner.

The compounds according to the present invention are, therefore, moreover, suitable in outstanding manner for the regulation of plant growth of various cultured species.

The compounds according to the present invention make possible a promotion of the vegetative growth of cultured plants, but also their restraint in certain concentration ranges. In other respects it is possible to obtain defined multiple yields by means of an influencing of the generative phase.

Under determined conditions these compounds can even display an anti-stress activity.

Since the compounds according to the present invention cause not only qualitative and quantitative alterations of the plants, but also changes in the metabolism in the plants, they are categorized in the class of Plant Growth Regulators, which distinguish by means of the following use possibilities:

Restraint of the vegetative growth of woody and weed plants, for example, at road borders, railroad plants and the like, in order to prevent too voluptuous growth. Growth restraint with grain, in order to prevent depositing or snapping off; with cotton, to increase the yield.

Influencing the branching of vegetative and generative organs with ornamental and cultured plants for augmenting the onset of blooming; or with tobacco and tomato in order to restrain the appearance of side-shoots.

Improvement of the fruit quality, for example, an increase in the sugar content of sugar beets, sugar cane or fruits, and a more uniform ripening of the harvesting goods, which leads to higher yields.

Increasing the resistance against stress, thus for example, against climatic influences such as cold and dryness; but also against phytotoxic influence of chemicals.

Influencing the latex flow of rubber plants.

Formation of parthenocarpic fruit, pollen sterility and sexual influences are likewise use possibilities for the compounds according to the present invention.

Control of the germination of seeds or the driving-out of buds.

Defolation or influence of the fruit fall in order to facilitate harvesting.

The compounds according to the present invention are are suitable in particular for the influencing of the vegetative and generative growth of several legumes, such as for example, soy beans and beta-beets.

Indeed according to the purpose of use, the amounts to be employed range generally between about 0.001 and 1 kg. active substance per hectare. If necessary, even greater application amounts can be employed.

The time of use is directed according to the purpose of use and the climatic conditions.

The compounds characterized by general formula I, the substituents can, for example, signify the following:

$R_1$ is hydrogen, $C_1-C_4$-alkyl, for example, methyl, ethyl, propyl, isopropyl, or butyl;

$R_2$ is $C_1-C_4$-alklyl, for example methyl, ethyl or propyl, cycloalkyl with 5 to 8 carbon atoms, for example, cyclopentyl, cyclohexyl, methylcyclohexyl; aryl, such as for example, phenyl, halophenyl, $C_1$–$C_4$-alkylphenyl, $C_1$–$C_4$-alkoxyphenyl, such as for example, methoxyphenyl, nitrophenyl, trifluoromethylphenyl or 2-pyridyl.

Under the groups designated by $R_3$ in the general formula I are to be understood for example, as if necessary substituted $C_1$–$C_{10}$-alkyl group, methyl, ethyl, propyl, isopropyl, n-butyl, sobutyl, sec-butyl, tert-butyl, pentyl, hexyl, heptyl, octyl, nonyl, decyl, 3,3-dimethylpropyl, chloromethyl, fluoromethyl, 2-chloroethyl, 2-hydroxyethyl, 2-methylsulfonyloxyethyl, 2-acetoxyethyl, methoxymethyl, 2-methoxyethyl, 2-ethoxyethyl, 2-phenoxyethyl, 2-(2,4-dichlorophenoxy)-ethyl, 2-(4-chlorophenoxy)ethyl, 2-dimethylamino-ethyl, 3-chloropropyl, 3-methoxypropyl, (2-methyl1,3-dioxolan-2-yl)-methyl, 3-dimethylaminopropyl, 3-phenoxypropyl, 2,2-dichlorocyclopropylmethyl; as $C_2$–$C_6$-alkenyl groups, ethenyl, 2-propenyl, 3-methyl-2-buten-1-yl, 2-methyl-1-propen-3-yl, hexenyl, heptenyl, octenyl; as $C_3$–$C_6$-alkinyl groups, 2-propinyl, butinyl, pentinyl, hexinyl;

As aliphatic-aromatic hydrocarbon groups, benzyl, 2-fluorobenzyl, 3-fluorbenzyl, 4-fluorobenzxyl, 2-chlorobenzyl, 4-chlorobenzyl, 2-bromobenzyl, 3 bromobenzyl, 4-bromobenzyl, 2,4-dichlorobenzyl, 2,5-dichlorobenzyl, 3,4-dichlorobenzyl, 2-methylbenzyl, 3-methylbenzyl, 4-methylbenzyl, 2-nitrobenzyl, 3-nitrobenzyl, 4-nitrobenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 2-ethoxybenzyl, 3-ethoxybenzyl, 4-athoxybenzyl, 2-propoxybenzyl, 3-propoxybenzyl, 4-propoxybenzyl, 2-butoxybenzyl, 4-butoxybenzyl, 2-methylthiobenzyl, 3-methylthiobenzyl, 4-methylthiobenzyl, 2-ethylthiobenzyl, 3-ethylthiobenzyl, 4-ethylthiobenzyl, 2-butylthiobenzyl, 3-butylthiobenzyl, 4-butylthiobenzyl.

X represents an oxygen or a sulfur atom.

As inorganic and organic acids for the formation of the acid addition salt mention may be made by way of example, of the hydrogen/halogen acids, such as for example hydrochloric acid and hydrobromic acid, moreover, phosphoric acid, sulfuric acid and nitric acid, mono- and bi- functional carboxylic acids and hydroxycarboxyl acids, such as for example acetic acid, maleic acid, succinic acid, furmaric acid, tartaric acid, citric acid, salicylic acid, sorbic acid, lactic acid, as well as sulfonic acids, such as for example, p-toluene, sulfonic acid and 1.5-naphthalene disulfonicacid.

These acid addition salts can be obtained according to the customary salt-formation techniques, such as for example, by dissolving a compound of formula I in a suitable solvent and then addition of the acid.

Of the compounds according to the present invention distinguishing by a growth-regulatory and defoliating activity in particular are those for which in the general formula I the group $R_1$ is hydrogen or methyl, $R_2$ is phenyl, 2-pyridyl and $R_3$ is methyl, ethyl, propyl, isopropyl, butyl, pentyl and hexyl.

Those compounds according to the present invention that have proven to be of most outstanding activity are the following:

3-(2-methyl-1,2,3-thiadiazol-3-in-5-yliden)-1-phenyl-urea, 3-(2-ethyl-1,2,3-thiadiazol-3-in-5-yliden)-1-phenyl-urea, hydrochloride, 3-(2-ethyl-1,2,3-thiadiazol-3-in-5-ylden)-1-phenyl-urea, 3-(2-propyl-1,2,3-thiadiazol-3-in-5-yliden)-1-phenyl-urea, 3-(2-butyl-1,2,3-thiadiazol-3-in-5-yliden)-1-phenyl-urea, 3-(2-methyl-1,2,3-thiadiazol-3-in-5-yliden)-1-phenyl-urea, hydrochloride, 3-(2-butyl-1,2,3-thiadiazol-3-in-5-yliden)-1-phenyl-urea, hydrochloride, 3-(2-isopropy,-1,2,3-thiadiazol-3-in-5-yliden)-1-phenyl-urea, 3-(2-ethyl-1,2,3-thiadiazol-3-in-5-yliden)-1-phenyl-urea.

The compounds according to the present invention can be used either alone, in mixture with one another, or with other active substances. If necessary, other plant protection or pest control agents can be added, indeed according to the desired purpose.

To the extent that a broadening of the activity spectrum is intended, also other biocides can be added. For example, suitable as herbicidally-effective mixture partners are those substances which are listed in Weed Abstracts, vol.31, no.7, 1982, under the title "Lists of Common Names and Abbreviations Employed for Currently Used Herbicides and Plant-growth Regulators in Weed Abstracts". In addition non-cytotoxic agents can be employed, which together with herbicides and/or growth-regulators, can provide a synergestic increase in activity, such as among others, wetters, emulsifiers, solvents and oily additives.

Phospholipids can also be employed as mixture partners, for example those from the groups, phosphatidylcholine, the hydrated phosphatidylcholines, phosphatidylethanolamine,, the N-acyl-phosphatidylethanolamines, phosphatidylinosite, phosphatidylserine, lysolecithin and phosphatidylglycerol.

Expediently, the characterized active substances or their mixtures are employed in the form of preparations such as powders, spray agents, granulates, solutions, emulsions or suspensions, with the addition of liquid and/or solid carrier materials or diluting agents and, if necessary, wetting, adhering, emulsifying and/or dispersing adjuvants.

Suitable liquid carrier substances include, for example, water, aliphatic and aromatic hydrocarbons, such as benzene, toluene, xylene, cyclohexanone, isophoron, dimethylsulfoxide, dimethylformamide, and moreover, mineral oil fractions and plant oils.

As solid carrier substances the following are suitable: mineral earths, for example, tonsil, silica gel, talc, kaolin, attapulgite, limestone, silicic acid and plant products, for example, meal.

As surface-active substances may be mentioned: for example, calcium, lignin sulfonate, polyoxyethylenealkylphenylether, naphalenesulfonic acids and their salts, phenylsulfonic acids and their salts, formaldehyde condensate, fatty alcohol sulfate as well as substituted benzene sulfonic acids and their salts.

To the extent that the active substances are supposed to be employed for the blanching of seed goods, then dyes can be admixed in order to provide the product seed goods a clearly visible coloration.

The portion of the active substance(s) in the different preparations can vary within broad limits. For instance, the compositions can contain about 10 to 90 percent by weight active substance, about 90 to 10 percent by weight liquid or solid weight carrier material, as well as up to, if necessary, 20 percent by weight surface-active substances with a corresponding reduction in the amount of carrier.

The application of the composition can follow in the customary manner, for example with water as carrier in spray brew amounts of about 100 up to 1000 liter/ha. An employment of the compositions in so-called low-volume or ultra-low-volume techniques is likewise possible, as is their application in the form of so-called micro-granulates.

The following components are presented by way of example to illustrate preparation of the compositions according to the present invention:

A. Spray Powder (a)

80% by weight active substance
15% by weight kaolin
5% by weight surface-active substance based upon the sodium salt of N-methyl-N-oleyl-taurine and the calcium salt of lignin sulfonic acid.

(b)

50% by weight active substance
40% by weight clay minerals
5% by weight cell pitch
5% by weight surface-active substance based upon a mixture of the calcium salt of lignin sulfonic acid with alkylphenolpolyglycolether.

(c)

20% by weight active substance
70% by weight clay minerals
5% by weight cell pitch
5% by weight surface-active substance based upon a mixture of the calcium salt of lignin sulfonic acid with alkylphenolpolyglycolether.

(d)

5% by weight active substance
80% by weight tonsil
10% by weight cell pitch
5% by weight surface-active substance based upon a fatty acid condensation product.

B. Emulsion Concentrate

20% by weight active substance
40% by weight xylene
35% by weight cyclohexanone
5% by weight mixture of nonylphenylpolyoxyethylene or calciumdodecylbenzenesulfonate

C. PASTE

45% by weight active substance
5% by weight sodium aluminum silicate
15% by weight cetylpolyglycolether with 8 mol ethylenoxide
2% by weight spindle oil
10% by weight polyethyleneglycol
23 parts water The new compounds according to the present invention, not previously described in the literature, can be prepared, for example, as follows:

(A) Metal compounds of the general formula

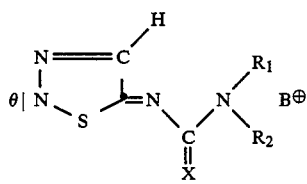

II can be reacted with compounds of the general formula $$R_x-Z \qquad \text{III}$$

if necessary in the presence of a solvent and if necessary in the presence of a catalyst or, (B) 1,2,3-thiadiazol-5-yl-urea of the general formula

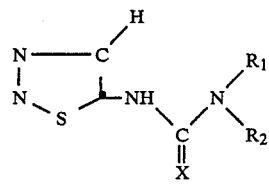

IV is reacted with compounds of the general formula $$R_3-Z \qquad \text{III}$$

if necessary in the presence of acid-binding agent, as well as if necessary in the presence of a suitable catalyst, wherein $R_1$, $R_2$, $R_3$ and X have the above given meaning. Z is a halogen atom or the group $R_3OSO_2$-O and B is a univalent metal equivalent.

Suitable as halogen in accordance with the present invention are, for example, chlorine, bromine, or iodine; suitable as alkyloxysulfonyloxy group are the methyl-, ethyl- and the propyloxysulfonyloxy groups. Suitable univalent metal equivalents are preferably a sodium or a lithium atom.

The reaction B can be performed not only if necessary in the presence of a solvent, not only with an excess of alkylation agent $R_3$—Z without acid-binding agent, but also in connection with an addition of a strong base.

If the addition of base is to be avoided one obtains then the compounds according to the present invention directly in the form of their additioned salts, from which moreover through use of stronger base, the compounds according to the present invention of formula I can be liberated.

The reaction of the reactants follows at temperatures between about −10 and 150° C., generally however, between room temperature and reflux temperature of the corresponding reaction mixture.

The duration of reaction amounts generally between 1 and 72 hours. As a rule, the reactions follow at normally pressure or slight excess pressure. The reactants are employed in about equimolar amounts for synthesis of the compounds according to the present invention. Suitable reaction media include solvents inert with respect to the reactants. The selection of solvent or suspension agent is directed according to the employment of the corresponding alkylhalogenoid as well as dialkylsulfate and the employed acid acceptor. As solvent or suspension agent, mention may be made, by way of example, of the following:

aliphatic and aromatic hydrocarbons, such as petroleum, ether, cyclohexane, hexane, heptane, benzene, toluene, zylol; halogenated hydrocarbons such as methylenechloride, ethylene chloride, chlorobenzene, chloroform, carbon tetrachloride, tetrachloroethylene; ethers such as diethylether, diisopropylether, anisol, dioxane, tetrahydrofuran, ethyleneglycoldiethylether, diethyleneglycoldiethylether; carboxylic acid nitriles such as acetonitrile, propionitrile; carboxylic acid amides such as dimethylformamide, dimethylacetamide, N-methylpyrrolidon, tetramethylurea, dimethylsulfoxide; ketones such as acetone, diethylketone, methylethylketone; alcohols such as methanol, ethanol, propanol, butanol and mixtures of such solvents with one another.

In several cases the reaction partners themselves can also serve as solvents.

Suitable as acid acceptors are organic bases, such as for example, triethylamine, trimethylamine, N,N-dimethylaniline, pyridine and pyridine bases (4-dimethylaminopyridine) or inorganic bases such as oxides, hydroxides, hydrides, carbonates, hydrogen carbonates and alcoholates of alkali- and earth alkali metals as well as amides and alkali salts of carboxylic acids (KOH, NaOH, Na$_2$CO$_3$, CH$_3$COONa, NaH, KH, LiH, CaH$_2$).

Liquid bases such as pyridine can simultaneously be employed as solvents. Any arising hydrogen halide can in many cases also by means of a throughput of inert gas, for example, nitrogen, be removed from the reaction mixture or be adsorbed with molecular sieve.

The presence of a reaction catalyst can often be of advantage. Suitable catalysts according to the present invention include potassium iodide and onium compounds, such as quaternary ammonium, phosphonium and arsonium compounds, as well as sulfonium compounds.

Likewise suitable are polyglycol ethers, particularly cyclicals such as for example, 18-crown-6 and tertiary amines, such as for example tributylamine. Preferred compounds are quaternary ammonium compounds, such as for example benzyltriethylammoniumchloride and tetrabutylammoniumbromide.

The compounds according to the present invention prepared by the abovedescribed method can be isolated from the mixture from the customary techniques, for example by distilling off of the employed solvent at normal or decreased pressure, by precipitation with water or by extraction.

An increased degree of purity can be obtained as a rule by means of column chromatographical purifiction as well as through fractionating crystallization.

With the employment of quicker alkylation techniques one obtains as a rule, in addition to the compounds according to the present invention, by-products in various measure. By means of suitable reaction conditions, if necessary by means of selection of suitable catalysts, it is possible to effect within the sense of the desired compounds according to the present invention a regioselective alkylation.

The compounds according to the present invention represent as a rule nearly colorless, odorless, crystalline bodies, which are with difficulty soluble in water and aliphatic hydrocarbons, moderately to well-soluble in halogenated hydrocarbons such as chloroform and carbon tetrachloride, ketones such as acetone, carboxylic acid amides such as dimethylformamide, sulfoxides such as diethylsulfoxide, carboxylic acid nitriles such as acetonitrile and lower alcohols such as methanol and ethanol.

Serving in particular as suitable solvent for recrystallization are carbon tetrachloride, chloroform, acetonitrile, toluene.

Starting products for production of the compounds according to the present invention are known per se or can be prepared according to customary techniques.

The novel features which are considered characteristic for the invention are set forth in particular in the appended claims. The invention itself, both as to its construction and procedure and method of operation and use, together with additional objects and advantages thereof, will be best understood from the following description of specific embodiments.

DESCRIPTION OF THE PREFERRED EMBODIMENTS

The following Examples illustrate preparation of the compounds according to the present invention.

EXAMPLE 1

3-(2-propyl-1,2,3-thiadiazol-3-in-5-yliden)-1-phenylurea 44.0 g (0.2 mol) 1-phenyl-3-(1,2,3-thiadiazol-5-yl)-urea are dissolved in 200 ml water-free dimethylformamide and carefully reacted with 8.0 g (0.2 mol) of a 55% dispersion of sodium hydride in oil. During the addition of the mixture, it is maintained by cooling at 30° C., subsequently after-stirred for 45 mins. at room temperature until hydrogen no longer develops. Thereafter and within a period of 15 mins. is added dropwise a solution of 22.47 ml (0.23 mol) n-propyliodide in 400 ml dimethylformamide, whereby the reaction temperature is not supposed to rise above 20° C. After the end of the addition the mixture is after-stirred yet 6 hours at room temperature. Thereupon the reaction mixture is carefully cast into 1000 ml icewater; subsequently it is extracted three times, each with 500 ml methylene chloride. The methylene chloride extracts are washed with a solution of 8.0 g sodium hydroxide in 80 ml water, then dried across magnesium sulfate, filtered and compressed in a vacuum.

In this manner are obtained 55 g of weakly yellow-colored crystals.

Further purification is effected column chromatographically (moderate pressure) in silica gel (eluent: diisopropylether/acetic ester 60:40).

The obtained products are nearly colorless crystals which can be recrystallized from diisopropylether.

Yield: 20.0 g =38.2% 3-(2-propyl-1,2,3-thiadiazol-3-in-5-yliden)-1-phenylurea

MP: 95° C.

DC: Flowing agent=ethyl acetate $R_f$-value: 0.670

Analysis: Calculated: C 54.94%; H 5.36%; N 21.36%; Found: C 55.14%; H 5.49%; N 21.41%.

EXAMPLE 2

3-(2-propyl-1,2,3-thiadiazol-3-in-5-yliden)-1-phenylurea hydrochloride 6.76 g (0.026 mol) 3-(2-propyl-1,2,3-thiadiazol-3-in-5-yliden)-1-phenylurea are dissolved in 180 ml acetone. To this is then added dropwise at 0° C. 8.6 ml (0.052 mol) of a saturated etheric hydrogen chloride solution. Reaction mixture is then after-stirred yet 15 mins. at room temperature. In order to complete the precipitation the reaction mixture is reacted still with 30 ml diisopropylether. The product weakly yellow-colored crystalled are evacuated in a vacuum, after-washed with 50 ml diisopropylether and then dried.

Yield: 6.4 g =87.5% 3-(2-propyl-1,2,3-thiadiazol-3-in-5-yliden)-1-phenylurea hydrochloride

MP: 188°–190° C.

DC: Flowing agent=ethyl acetate $R_f$-value 0.615

Analysis: Calculated; C 48.23%; H 5.06%; N 18.75%; Found: C 47.95%; H 5.12%; N 18.54%.

EXAMPLE 3

3-(2-ethyl-1,2,3-tbiadiazol-3-in-5-yliden)-1-phenylurea (a) 11.0 g (0.05 mol) 1-phenyl-3-(1,2,3-thiadiazol-5-yl)-urea are suspended in 200 ml dry ethyleneglycoldiethylether. At first are added 2.6 g (0.01 mol) 18-crown- 6, and thereafter the reaction mixture is carefully reacted with 2.4 g (0.05 mol) of a 50% dispersion of sodium hydride in oil, whereby the reaction temperature is not supposed to rise above 30° C.

Subsequently the mixture is after-stirred yet 2 hours at room temperature. To the in-the-meantime clear solution is added dropwise within 15 mins. a solution of 4.0 ml (0.06 mol) ethyliodide in 20 ml ethyleneglycoldiethylether at 25° C. Subsequent to the end of this addition, the reaction mixture is after-stirred yet 8 hours at room temperature. The nearly-clear solution is evaporated in a vacuum at 40° C. The residue is withdrawn in 200 ml methylenechloride; the organic phase is then washed with a solution of 2 g sodium hydroxide in 20 ml water. The methylenechloride extract, washed with 100 ml water, is dried across magnesium sulfate filtered and compressed in a vacuum. One obtains in this manner 13.0 g weakly-yellow crystals which are recrystallized from diisopropylether.

Yield: 6.38 g =51.5% 3-(2-ethyl-1,2,3-thiadiazol-3-in-5-yliden)-1-phenylurea

MP: 123°–124° C.

DC: Flowing agent ethyl acetate $R_f$-value: 0.610

Analysis: Calculated: C 53.21%; H 4.87%; N 22.56%; Found: C 53.46%; H 5.11%; N 22.58%.

(b) 11.0 g (0.05 mol) 1-phenyl-3-(1,2,3-thiadiazol-5-yl)-urea are dissolved in a solution of 5.92 g (0.09 mol) potassium hydroxide in 30 ml water. To this are added dropwise within 30 mins. at about 30 C 9.82 ml diethylsulfate. The reaction mixture is after-stirred initially 30 mins. at room temperature. It is then heated yet 30 mins. to 60° C. Subsequently the reaction mixture is extracted three times, each with 200 ml methylene chloride. The methylene chloride extract, filtered and dried across magnesium sulfate, is compressed in a vacuum. One obtains in this manner 11.4 g yellowish crystals which are recrystallized from diisopropylether.

Yield: 4.96 g =40.0% 3-(2-ethyl-1,2,3-thiadiazol-3-in-5-yliden)-1-phenylurea

MP: 123°–124° C.

DC: Flowing agent=ethyl acetate $R_f$-value: 0.610

In analogous manner the further compounds according to the present invention are prepared:

| EXAMPLE | NAME OF THE COMPOUND | PHYSICAL CONSTANT |
|---|---|---|
| 4 | 3-(2-methyl-1,2,3-thiadiazol-3-in-5-yliden)-1-phenyl urea | MP: 175–178° C. |
| 5 | 3-(2-(2,6-dichlorobenzyl)-1,2,3-thiadiazol-3-in-5-yliden)-1-henyl-urea | MP: 177° C. |
| 6 | 3-(2-(4-chlorobenzyl)-1,2,3-thiadiazol-3-in-5-yliden)-1-phenylurea | MP: 154° C. decomp. |
| 7 | 3-(2-chlorobenzyl)-1,2,3-thiadiazol-3-in-5-yliden)-1-phenylurea | MP: 146° C. |
| 8 | 3-(2-4,dichlorobenzyl)-1,2,3-thiadiazol-3-in-5-yliden)-1-phenylurea | MP: 140–142° C. |
| 9 | 3-(2-ethyl-1,2,3-thiadiazol-3-in-5-yliden)-1-phenylurea hydrochloride | MP: 197° C. decomp. |
| 10 | 3-(2-butyl-1,2,3-thiadiazol-3-in-5-yliden)-1-phenylurea | MP: 91–92° C. |
| 11 | 3-(2-methyl-1,2,3-thiadiazol-3-in-5-yliden)-1-phenylurea hydrochloride | MP: 211° C. decomp. |
| 12 | 3-(2-butyl-1,2,3-thiadiazol-3-in-5-yliden)-1-phenylurea hydrochloride | MP: 188–189° C. decomp. |
| 13 | 3-(2-isopropyl-1,2,3-thiadiazon-3-in-5-yliden)-1-phenylurea | MP: 126–127° C. |
| 14 | 3-(2-propenyl)-1,2,3-thiadiazol-3-in-5-yliden)-1-phenylurea | MP: 131° C. |
| 15 | 1-phenyl-3-(2-propinyl)-1,2,3-thiadiazol 3-in-5-yliden)-urea | MP: 157° C. |
| 16 | 3-(2-benzyl-1,2,3-thiadiazol-3-in-5-yliden)-1-phenylurea | MP: 141° C. |
| 17 | 3-(2-(2-chloroethyl)-1,2,3-thiadiazol-3-in-5-yliden)-1-phenylurea | MP: 135° C. |
| 18 | 3-(2-2-acetoxyethyl)-1,2,3-thiadiazol-3-in-5-yliden)-1-phenylurea | MP: 93.5–94° C. |
| 19 | 3-(2-decyl-1,2,3-thiadiazol-3-in-5-yliden)-1-phenylurea | MP: 78–80° C. |
| 20 | 3-(2-ethenyl-1,3,4-thiadiazol-3-in-5-yliden)-1-phenylurea | MP: 166–167° C. |
| 21 | 3-(2-methoxymethyl-1,2,3-thiadiazol-3-in-5-yliden)-1-phenylurea | MP: 88–89° C. |
| 22 | 3-(2-ethyl-1,2,3-thiadiazol-3-in-5-yliden)-1-methyl-1-phenylurea | $n_D^{20}$: 1.6602 |
| 23 | 1-ethyl-3-(2-ethyl-1,2,3-thiadiazol-3-in-5-yliden)-1 phenylurea | MP: 70–73° C. |

The following operational examples serve for illustration of various use possiblities for the compounds according to the present invention and which follow in the form of the above set forth preparations.

EXAMPLE 21

Young cotton plants in the stage of 4 to 6 developed leaf pairs are treated with the active substances set forth in the table below (4×repetition). The applied spray brew amounts correspond to 500 liters/ha. The plants are maintained in a greenhouse as a rule at temperatures of between 19°–22° C. Three weeks after the application the percentage of fallen leaves is determined. The results are set forth in the following table.

| COMPOUNDS ACCORDING TO THE PRESENT INVENTION | DOSE IN g ACTIVE SUBSTANCE/Ha | DEFOLIATION IN % |
|---|---|---|
| 3-(2-methyl-1,2,3-thiadiazol-3-in-5-yliden)-1-phenylurea | 500 | 90 |
| 3-(2-ethyl-1,2,3-thiadiazol-3-in-5-yliden)-1-phenylurea hydrochloride | 500 | 100 |
| 3-(2-ethyl-1,2,3-thiadiazol-3-in-5-yliden(-1-phenylurea | 500 | 100 |
| 3-(2-propyl-1,2,3-thiadiazol-3-in-5-yliden(-1-phenylurea | 500 | 100 |
| 3-(2-butyl-1,2,3-thiadiazol-3-in-5-yliden(-1-phenylurea | 500 | 100 |
| 3-(2-methyl-1,2,3-thiadiazol-3-in-5-yliden)-1-phenylurea hydrochloride | 500 | 95 |
| 3-(2-propyl-1,2,3-thiadiazol-3-in-5-yliden(-1-phenylurea hydrochloride | 500 | 95 |
| 3-(2-butyl-1,2,3-thiadiazol-3-in-5-yliden)-1-phenylurea hydrochloride | 500 | 90 |
| 3-(2-isopropyl-1,2,3-thiadiazol-3-in-5-yliden)-1-phenylurea | 500 | 100 |
| 3-(2-(2-propenyl)-1-2,3-thiadiazol-3-in-5-yliden)-1-phenylurea | 500 | 80 |
| 1-phenyl-3-(2-(2-propinyl)-1,2,3-thiadiazol-3-in-5-yliden)-10-phenyl-urea | 500 | 75 |
| 3-(2-(2-chloroethyl)-1,2,3-thiadiazol-3-in-5-yliden)-1-phenylurea | 500 | 75 |
| 3-(2-ethenyl-1,2,3-thiadiazol-3-in-5-yliden)-1-phenylurea | 500 | 96 |
| 3-(2-methoxymethyl-1,2,3-thiadiazol-3-in-5-yliden)-1-phenylurea | 500 | 100 |
| 3-(2-ethyl-1,2,3-thiadiazol-3-in-5-yliden)-1-methyl-1-phenylurea | 500 | 100 |

EXAMPLE 22

Young cotton plants at the stage of 5 to 6 developed pairs are treated as in Example 21 and then evaluated after 7 days, i.e, the percentage of shed leaves is determined:

| COMPOUNDS ACCORDING TO THE PRESENT INVENTION | DOSE IN g ACTIVE SUBSTANCE | DEFOLIATION IN % |
|---|---|---|
| 3-(2-methyl-1,2,3-thiadiazol-3-in-5-yliden)-1-phenylurea | 40 | 90 |
| 3-(2-ethyl-1,2,3-thiadiazol-3-in-5-yliden)-1-phenylurea hydrochloride | 40 | 90 |
| 3-(2-ethyl-1,2,3-thiadiazol-3-in-5-yliden)-1-phenylurea | 40 | 95 |
| 3-(2-propyl-1,2,3-thiadiazol-3-in-5-yliden)-1-phenylurea | 40 | 85 |
| 3-(2-butyl-1,2,3-thiadiazol-3-in-5-yliden)-1-phenylurea | 40 | 85 |
| 3-(2-methyl-1,2,3-thiadiazol-3-in-5-yliden)-1-phenylurea hydrochloride | 40 | 80 |
| 3-(2-propyl-1,2,3-thiadiazol-3-in-5-yliden)-1-phenylurea hydrochloride | 40 | 85 |
| 3-(2-butyl-1,2,3-thiadiazol-3-in-5-yliden)-1-phenylurea hydrochloride | 40 | 84 |
| 3-(2-isopropyl-1,2,3-thiadiazol-3-in-5-yliden)-1-phenylurea | 40 | 62 |
| 3-(2-(2-propenyl)-12,3-thiadiazol-3-in-5-yliden)-1-phenylurea | 40 | 52 |
| 3-(2-ethenyl-1,2,3-thiadiazol-3-in-5-yliden)-1-phenylurea | 40 | 62 |
| Comparison agent according to DE-OS 2214632 and 2506690 | | |
| 1-phenyl-3-(1,2,3-thiadiazol-5-yl)-urea | 40 | 38 |

EXAMPLE 23

Young cotton plants in the stage of 5 to 6 developed leaves are treated as in Example 21 and maintained in a greenhouse at temperatures between about 20 and 25° C. Five days and three weeks after the application the percentage of shed leaves is determined. The resulting values enable a quick recognition of the defoliation of the plants by means of the compounds according to the present invention.

| COMPOUNDS ACCORDING TO THE PRESENT INVENTION | DOSE IN g ACTIVE SUBSTANCE | DEFOLIATION AFTER 5 days | 22 days |
|---|---|---|---|
| 3-(2-ethyl-1,2,3-thiadiazol-3-in-5-yliden)-1-phenylurea hydrochloride | 80 | 57 | 100 |
| 3-(2-ethyl-1,2,3-thiadiazol-3-in-5-yliden)-1-phenylurea | 80 | 38 | 100 |
| 3-(2-propyl-1,2,3-thiadiazol-3-in-5-yliden)-1-phenylurea | 80 | 43 | 100 |
| 3-(2-propyl-1,2,3-thiadiazol-3-in-5-yliden)-1-phenylurea hydrochloride | 80 | 33 | 100 |
| Comparison agent according to DE-OS 2214632 and 2506690 | | | |
| 1-phenyl-3-(1,2,3-thiadiazol-5-yl)-urea | 80 | 10 | 90 |

EXAMPLE 24

Seeds of *Amaranthus caudatus* are placed in a Petrie dish with a filter-paper disk and 5 ml phosphate buffer (1 mM, pH 6.8) and allowed to germinate. Thirty seeds are distributed uniformly onto the dried filter paper; the germination solution contains the formulated active substance and 1 g tyrosine/1. After the placement of the seeds, the Petrie dishes are placed in the dark. (25° C., 70% relative air moisture.) After 4 days the red coloration of the seedlings is classified as an indication for a cytokinetic-like effect:

0 = as control
1 = weak red coloration
2 = moderate red coloration
3 = strong red coloration
4 = very strong red coloration, shortened roots, highest cytokinetic activity

| COMPOUNDS ACCORDING TO THE PRESENT INVENTION | MOLARITY OF THE TEST SOLUTION (M) | CLASSIFICATION |
|---|---|---|
| 3-(2-ethyl-1,2,3-thiadiazol-3-in-5-yliden)-1-phenylurea hydrochloride | $10^{-7}$ | 3 |
| | $10^{-8}$ | 4 |
| 3-(2-ethyl-1,2,3-thiadiazol-3-in-5-yliden)-1-phenylurea | $10^{-7}$ | 4 |
| | $10^{-8}$ | 3 |
| 3-(2-propyl-1,2,3-thiadiazol-3-in-5-yliden)-1-phenylurea | $10^{-7}$ | 3 |
| | $10^{-8}$ | 0 |
| 3-(2-isopropyl-1,2,3-thiadiazol-3-in-5-yliden)-1-phenylurea | $10^{-7}$ | 4 |
| | $10^{-8}$ | 4 |

The results show that the compounds according to the present invention still evoke a clear cytokinetic effect even in very low concentrations.

EXAMPLE 25

Soy bean plants are treated with the substances according to the present invention in an after-germination technique and then placed in a greenhouse. The concentration of the active substances amounts calculated to 10 g/Ha. After 6 days disks are punched out from the primary leaves, the chlorophyll obtained therein is extracted and then determined photometrically. The so-obtained chlorophyll contents are normalized in relation to the control.

| COMPOUNDS ACCORDING TO THE PRESENT INVENTION | CHLOROPHYLL ENRICHMENT IN COMPARISON TO THE CONTROL (%) |
|---|---|
| 3-(2-decyl-1,2,3-thiadiazol-3-in-5-yliden)-1-phenylurea | 112.6 |
| 3-(2-(2-acetoxyethyl)-1,2,3-thiadiazol-3-in-5yliden)-1-phenylurea | 124.9 |
| 3-(2-(2-chlorethyl)-1,2,3-thiadiazol-3-in-5-yliden)-1-phenylurea | 109.9 |
| 3-(2-benzyl-1,2,3-thiadiazol-3-in-5-yliden)-1-phenylurea | 126.8 |
| 1-phenyl-2-(2-(2-propinyl)-1,2,3-thiadiazol-3-in-5-yliden)-urea | 129.4 |
| 3-(2-propyl-1,2,3-thiadiazol-3-in-5-yliden)-1-phenylurea | 117.2 |
| Control | 100.0 |

The substances according to the present invention thus cause even short times after the application a clear chlorophyll enrichment in the leaves.

EXAMPLE 26

Wheat seeds are swelled in an aqueous testing solution for 4 hours, in glass vessels. Thereafter, the vessels are provided with an aqueous solution of polyethyleneglycol 6,000, so that the solution in the vessels contains 22.5% polyethyleneglycol. The vessels are then covered with the lid of a Petrie dish, placed in a climate chamber at 25° C. and 70% relative air moisture, and then illuminated for 12 hours per day. After 1 week is determined the course of the germination. For this purpose the length of the shoots is measured (respectively the coleoptile or coleoptile and 1 leaf pair). The following table contains the results of the testing, in which after the addition to the polyethyleneglycol of the test substances 0.01, 0.001 and 0.0001 percent are obtained.

| COMPOUNDS ACCORDING TO THE PRESENT INVENTION | CONCENTRATION OF COMPOUND IN % | LENGTH OF SHOOTS |
|---|---|---|
| 1-phenyl-3-(2-(2-propinyl-1,2,3-thiadiazol-3-in-5-yliden urea | 0.01 | 3.8 |
|  | 0.001 | 1.9 |
|  | 0.0001 | 2.0 |
| 3-(2-benzylpl,2,3-thiadiazol-3-in-5-yliden)-1-phenylurea | 0.01 | 5.1 |
|  | 0.001 | 5.3 |
|  | 0.0001 | 1.1 |
| 3-(2-chloroethyl)-1,2,3-thiadiazol-3-in-5-yliden-1-phenylurea | 0.01 | 4.0 |
|  | 0.001 | 3.5 |
|  | 0.0001 | 2.0 |
| Control | — | 0.2 |

The results show that the control—which is only pre-swollen in tap water—is strongly restrained in growth by means of the osmoticum.

The seedlings, which were pre-treated with the substances according to the present invention, to the contrary grow despite the osmotic stress very much more quickly than the untreated control.

EXAMPLE 27

Soy bean plants are treated with the substances according to the present invention and in the primary leaf stage. Therewith calculated 10 g and 50 g active substance per Ha. are applied.

The plants are cultivated at 25° C. and 70% relative air moisture in a climatic chamber.

After 4 weeks the number of formed blooms and the onset of hulls is determined. These numbers are adjusted in relation to the control. Moreover, the degree of branching of the plants is determined according to a classification scale from 0 to 4, wherefor:

0 = branching as with the control
1 = weak promotion of branching
2 = moderate promotion of branching
3 = strong promotion of branching
4 = branching very strongly promoted in comparison to control Likewise determined in relation to the control is the growth reduction.

| COMPOUNDS ACCORDING TO THE PRESENT INVENTION | Concentration of active substance/Ha. | Growth reduction in % | Blooms & hulls | Branching |
|---|---|---|---|---|
| 3-(2-(2-acetoxyethyl)-1,2,3-thiadiazol-3-in-5-yliden)-1-phenylurea | 10 | 25 | 119 | 4 |
|  | 50 | 50 | 108 | 4 |
| Controls | — | 0 | 100 | 0 |

The substances according to the present invention intervened strongly in the material exchange physiology of the soy bean plants, which effects an increase in the number of formed blooms, an intensive branching and a reduction in growth.

It will be understood that each of the elements described above, or two or more together may also find a useful application in other types of plant regulation differing from the type described above.

While the invention has been illustrated and described as embodied in 1,2,3-thiadiazol-3-in-5-yliden-urea derivatives, processes for the production of these compounds as well as compositions containing the same and having growth-regulatory and defoliating activity, it is not intended to be limited to the details shown since various modifications and structural changes may be made without departing in any way from the spirit of the present invention.

Without further analysis, the foregoing will so fully reveal the gist of the present invention, that others can, by applying current knowledge, readily adapt it for various applications without omitting features, that from the standpoint of prior art, fairly constitute essential characteristics of generic or specific aspects of this invention.

What is claimed as new and desired to be protected by Letters Patent is set forth in the appended claims:

1. 1,2,3-thiadiazol-3-in-5-yliden-urea derivative of the general formula

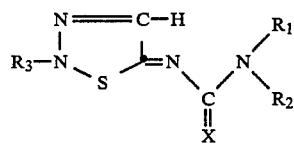

in which
$R_1$ is hydrogen, methyl, ethyl, propyl, isopropyl or butyl;
$R_2$ is methyl, ethyl, propyl, cyclopentyl, cyclohexyl, methylcyclohexyl, phenyl, halophenyl, nitrophenyl, trifluoromethylphenyl, methoxyphenyl or pyridyl;
$R_3$ is methyl, ethyl, proply, isopropyl, n-butyl, isobutyl, sec-butyl, tert-butyl, pentyl, hexyl, heptyl, octyl, nonyl, decyl, 3,3-dimethylpropyl, chloromethyl, fluoromethyl, 2-chloroethyl, 2-hydroxyethyl, 2-methylsulfonyloxyethyl, 2-acetoxyethyl, methoxymethyl, 2-methoxyethyl, 2-ethoxyethyl, 2-phenoxyethyl, 2-(2,4-dichlorophenoxy)-ethyl, 2-(4-chlorophenoxy)-ethyl, 2-dimethylaminoethyl, 3-chloropropyl, 3-methoxypropyl, (2-methyl-1,3-dioxolan-2-yl)-methyl, 3-dimethylamino propyl, 3-phenoxypropyl, 2,2-dichlorocyclopropylmethyl, ethenyl, 2-propenyl, 3-methyl-2-buten-1-yl, 2-methyl-1-propen-3-yl, hexenyl, heptenyl, octenyl, 2-propinyl, butinyl, pentinyl, hexinyl, benzyl, 2-fluorobenzyl, 4-fluorobenxyl, 2-chlorobenzyl, 2-bromobenzyl, 3-bromobenzyl, 4-bromobenzyl, 2,4-dichlorobenzyl, 3-methylbenzyl, 4-methylbenzyl, 2-nitrobenzyl, 3-nitrobenzyl, 4-nitrobenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 2-ethoxybenzyl, 3-ethoxybenzyl, 4-ethoxybenzyl, 2-propoxybenxyl, 3-propoxybenzyl, 4-propoxybenzyl, 2-butoxybenzyl, 3-butoxybenzyl, 4-butoxybenzyl, 2-methylthiobenzyl, 3-methylthiobenzyl, 4-methylthiobenzyl, 2-ethylthiobenzyl, 3-ethylthiobenzyl, 4-ethylthiobenzyl, 2-butylthiobenzyl, 3-butylthiobenzyl or 4-butylthiobenzyl; and X is an oxygen or a sulfur atom;

as well as its acid addition salts with an inorganic or an organic acid.

2. The compound according to claim 1 which is 3-(2-propyl-1,2,3-thiadiazol-3-in-5-yliden)-1-phenylurea.

3. The compound according to claim 1 which is 3-(2-propyl-1,2,3-thiadiazol-3-in-5-yliden)-1-phenylurea hydrochloride.

4. The compound according to claim 1 which is 3-(2-ethyl-1,2,3-thiadiazol-3-in-5-yliden)-1-phenylurea hydrochloride.

5. The compound according to claim 1 which is 3-(2-isopropyl-1,2,3-thiadiazol-3-in-5-yliden)-1-phenylurea.

6. The compound according to claim 1 which is 1-phenyl-3-(2-(2-propinyl)-1,2,3-thiadiazol-3-in-5-yliden)-urea.

7. The compound according to claim 1 which is 3-(2-ethyl-1,2,3-thiadiazol-3-in-5-yliden)-1-phenyl-urea.

8. The compound 3-(2-(2-acetoxyethyl)-1,2,3-thiadiazol-3-in-5-yliden-1-phenylurea.

9. A composition of matter having growth-regulatory and defoliating activity for plants, comprising at least one compound according to claim 1 in a suitable carrier means.

10. Composition according to claim 9, and containing about 10 to 90 percent by weight active substance and about 90 to 10 percent by weight liquid or solid carrier material with or without up to 20 percent by weight surface-active substance with a corresponding reduction in the amount of carrier.

11. Method for controlling the growth of plants, comprising applying onto or within the locus of said plants a growth-controlling effective amount of the composition according to claim 9.

12. The method according to claim 11, wherein said growth-controlling effective amount comprises from about 100 to 1000 liter/ha.

13. The method according to claim 11, wherein said composition is applied in the form of micro-granulates.

14. Method for the defoliation of plants, comprising applying onto or within the locus of said plants a defoliating effective amount of the composition according to claim 9.

15. The method according to claim 14, wherein said defoliating effective amount comprises from about 100 to 1000 liter/ha.

16. The method according to claim 14, wherein said composition is applied in the form of micro-granulates.

* * * * *